(12) United States Patent
Zeller

(10) Patent No.: US 6,194,463 B1
(45) Date of Patent: Feb. 27, 2001

(54) N-SULPHONYL AND N-SULPHINYL AMINO ACID AMIDES AS MICROBICIDES

(75) Inventor: Martin Zeller, Baden (CH)

(73) Assignee: Novartis Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/380,022

(22) PCT Filed: Feb. 23, 1998

(86) PCT No.: PCT/EF98/01028

§ 371 Date: Aug. 24, 1999

§ 102(e) Date: Aug. 24, 1999

(87) PCT Pub. No.: WO98/38160

PCT Pub. Date: Sep. 3, 1998

(30) Foreign Application Priority Data

Feb. 25, 1997 (CH) ........................................ 431/97

(51) Int. Cl.[7] .......................... A01N 41/12; A01N 41/06; A01N 41/02; A01N 37/18; A01N 37/34

(52) U.S. Cl. ...................... 514/607; 514/521; 514/531; 514/542; 514/600; 514/605; 514/608; 558/404; 560/13; 564/79; 564/99; 564/101; 564/102

(58) Field of Search ................... 564/79, 99, 101, 564/102; 560/13; 558/404; 514/521, 531, 542, 600, 605, 607, 608

(56) References Cited

U.S. PATENT DOCUMENTS 5,254,715 * 10/1993 Picard et al. ............................ 560/13
5,482,972 1/1996 Seitz et al. ............................ 514/487

FOREIGN PATENT DOCUMENTS 0 554 729 * 1/1993 (EP) .
0 554 729 8/1993 (EP) .
WO95/30651 11/1995 (WO) .
95/30651 * 11/1995 (WO) .

* cited by examiner

Primary Examiner—Peter O'Sullivan
(74) Attorney, Agent, or Firm—William A. Teoli, Jr.

(57) ABSTRACT

α-Amino acid amides of formula (I) wherein the substituents are defined as follows: n is a number zero or one; $R_1$ to $R_7$ are as defined herein; $R_8$ is $C_1$–$C_6$alkyl, $C_3$–$C_6$alkenyl or $C_3$–$C_6$alkynyl; $R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group (a) wherein p and q are identical or different and are each independently of the other a number zero or one; and $R_{13}$, $R_{14}$, $R_{15}$ and $R_{16}$ are identical or different and are each independently of the others hydrogen or $C_1$–$C_4$alkyl; X is hydrogen, in which case p and q must have the value zero; phenyl, unsubstituted or mono- or poly-substituted by halogen, nitro, cyano, carboxy, $C_2$–$C_6$alkenyl, $C_2$–$C_6$alkenyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$or by $C_1$–$C_6$alkoxy, cyano, —$COOR_{17}$; —$COR_{18}$ or a group (b) wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_2$–$C_6$alkenyl, $C_2$–$C_6$alkynyl or phenyl unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl, are valuable microbicides. They can be used in plant protection in the form of suitable compositions, for example, for controlling fungal diseases.

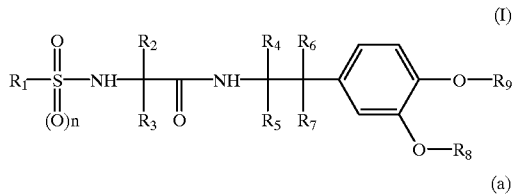

(I)

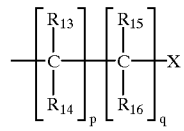

(a)

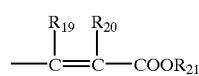

(b)

11 Claims, No Drawings

N-SULPHONYL AND N-SULPHINYL AMINO ACID AMIDES AS MICROBICIDES

This application is a 371 of pct/EP 98/01028 Feb. 23, 1998.

The present invention relates to novel α-amino acid amides of formula I below. It relates to the preparation of those substances and to agrochemical compositions comprising at least one of those compounds as active ingredient. The invention relates also to the preparation of the said compositions and to the use of the compounds or the compositions in controlling or preventing the infestation of plants by phytopathogenic microorganisms, especially fungi.

The compounds according to the invention correspond to the general formula I

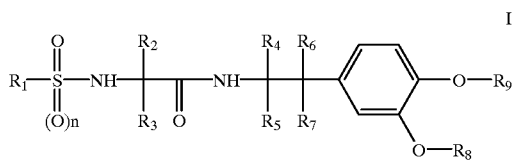

wherein the substituents are defined as follows:

n is a number zero or one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsufonyl, $C_3$–$C_8$cycloalkyl, cyano, $C_1$–$C_6$alkoxycarbonyl, $C_3$–$C_6$alkenyloxycarbonyl, $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl or a group $NR_{11}R_{12}$; wherein $R_{11}$ and $R_{12}$ are each independently of the other hydrogen, $C_1$–$C_6$alkyl or together are tetra- or penta-methylene;

$R_2$ is hydrogen, $C_1$–$C_8$alkyl;

$R_3$ is $C_3$–$C_8$cycloalkyl that is unsubstituted or may be substituted by $C_1$–$C_6$alkyl, hydroxy, $C_1$–$C_4$alkoxy, mercapto or by $C_1$–$C_4$alkylthio;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_8$cycloalkyl; a $C_1$–$C_6$alkyl-, $C_3$–$C_6$alkenyl- or $C_3$–$C_6$alkynyl-group each of which is substituted by one or more halogen atoms; or a group

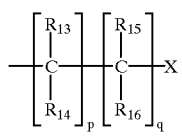

wherein p and q are identical or different and are each independently of the other a number zero or one; and $R_{13}$, $R_{14}$, $R_{15}$ and $R_{16}$ are identical or different and are each independently of the others hydrogen or $C_1$–$C_4$alkyl;

X is hydrogen, in which case p and q must have the value zero; phenyl, unsubstituted or mono- or poly-substituted, for example, by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alknyloxycarbonyl, $C_1$–$C_6$alkyl or by $C_1$–$C_6$alkoxy; cyano; —$COOR_{17}$; —$COR_{18}$ or a group

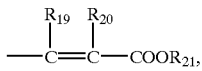

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_2$–$C_6$alkenyl, $C_2$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl.

An important group is formed by compounds of formula I wherein n is a number one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group $NR_{11}, R_{12}$;

wherein $R_{11}$ and $R_{12}$ are each independently of the other hydrogen, $C_1$–$C_6$alkyl or together are tetra- or penta-methylene;

$R_2$ is hydrogen;

$R_3$ is $C_3$–$C_7$cycloalkyl that is unsubstituted or may be substituted by $C_1$–$C_6$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

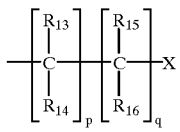

wherein p and q are identical or different and are each independently of the other a number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl, unsubstituted or substituted by halogen, nitro, cyano, $C_1$–$C_4$alkyl or by $C_1$–$C_4$alkoxy; cyano; —$COOR_{17}$; —$COR_{18}$ or a group

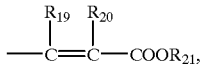

wherein $R_{17}$ and $R_{21}$, are each independently of the other hydrogen, $C_1$–$C_6$alkyl, $C_3$–$C_6$-alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (sub-group A).

An important group is formed by compounds of formula I wherein n is a number one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$;

wherein $R_{11}$ and $R_{12}$ are each independently of the other $C_1$–$C_6$alkyl or together are tetra- or penta-methylene;

$R_2$ is hydrogen; and $R_3$ is $C_3$–$C_7$cycloalkyl that is unsubstituted or may be substituted by $C_1$–$C_6$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

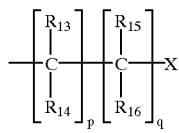

wherein p and q are identical or different and are each independently of the other a number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl, unsubstituted or substituted by halogen, nitro, cyano, $C_1$–$C_4$alkyl or by $C_1$–$C_4$alkoxy; cyano; —$COOR_{17}$; —$COR_{18}$ or a group

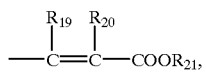

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (sub-group B).

Of special importance are compounds of formula I wherein n is a number one;

$R_1$ is $C_1$–$C_{12}$alkyl; $C_1$–$C_{12}$haloalkyl or a group $NR_{11}R_{12}$; wherein $R_{11}$ and $R_{12}$ are $C_1$–$C_6$alkyl;

$R_2$ is hydrogen; and $R_3$ is $C_3$–$C_7$cycloalkyl that is unsubstituted or may be substituted by $C_1$–$C_6$alkyl;

$R_4$ is hydrogen or $C_1$–$C_4$alkyl;

$R_5$, $R_6$ and $R_7$ are hydrogen;

$R_8$ is $C_1$–$C_6$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

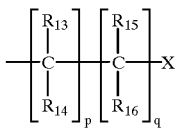

wherein p and q are identical or different and are each independently of the other a number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl, unsubstituted or substituted by halogen, nitro, cyano, $C_1$–$C_4$alkyl or by $C_1$–$C_4$alkoxy; cyano; —$COOR_{17}$; —$COR_{18}$ or a group

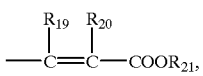

wherein $R_{17}$ and $R_{21}$ are each independently of the other hydrogen, $C_1$–$C_6$alkyl, $C_3$–$C_6$alkenyl or $C_3$–$C_6$alkynyl, and $R_{18}$ is hydrogen; $C_1$–$C_6$alkyl $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and $R_{19}$ and $R_{20}$ are identical or different and are each independently of the other hydrogen or $C_1$–$C_4$alkyl (sub-group Ba).

Another important group is formed by compounds of formula I wherein n is a number one;

$R_1$ is $C_1$–$C_4$alkyl or dimethylamino;

$R_2$ is hydrogen; and $R_3$ is $C_3$–$C_6$cycloalkyl that is unsubstituted or may be substituted by $C_1$–$C_4$alkyl;

$R_4$ is hydrogen or methyl;

$R_5$, $R_6$ and $R_7$ are hydrogen;

$R_8$ is $C_1$–$C_2$alkyl;

$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

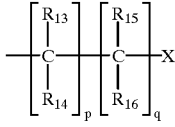

wherein p and q are identical or different and are each independently of the other a number zero or one; and $R_{13}$, $R_{14}$, $R_{15}$ and $R_{16}$ are identical or different and are each independently of the others hydrogen or $C_1$–$C_4$alkyl; and X is hydrogen, in which case p and q must have the value zero; phenyl, unsubstituted or substituted by halogen, nitro, cyano, $C_1$–$C_4$alkyl or by $C_1$–$C_4$alkoxy; cyano; —COOR$_{17}$; —COR$_{18}$ or a group

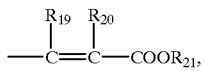

wherein
$R_{17}$ and $R_{21}$ are each independently of the other hydrogen, $C_1$–$C_6$alkyl, $C_3$–$C_6$alkenyl or $C_3$–$C_6$alkynyl, and
$R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and
$R_{19}$ and $R_{20}$ are identical or different and are each independently of the other hydrogen or $C_1$–$C_4$alkyl (sub-group Bb).

Preferred among those compounds are those wherein
n is a number one;
$R_1$ is $C_2$–$C_4$alkyl or dimethylamino;
$R_2$ is hydrogen; and
$R_3$ is cyclopropyl that is unsubstituted or may be substituted by $C_1$–$C_4$alkyl;
$R_4$ is hydrogen;
$R_5$, $R_6$ and $R_7$ are hydrogen;
$R_8$ is methyl;
$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

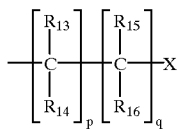

wherein
p and q are identical or different and are each independently of the other a number zero or one; and
$R_{13}$, $R_{14}$, $R_{15}$ and $R_{16}$ are identical or different and are each independently of the others hydrogen or $C_1$–$C_4$alkyl; and
X is hydrogen, in which case p and q must have the value zero; phenyl, unsubstituted or substituted by halogen, nitro, cyano, $C_1$–$C_4$alkyl or by $C_1$–$C_4$alkoxy; cyano; —COOR$_{17}$; —COR$_{18}$ or a group

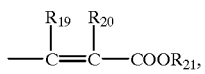

wherein
$R_{17}$ and $R_{21}$ are each independently of the other hydrogen, $C_1$–$C_6$alkyl, $C_3$–$C_6$alkenyl or $C_3$–$C_6$alkynyl, and
$R_{18}$ is hydrogen; $C_1$–$C_6$alkyl, $C_3$–$C_6$alkenyl, $C_3$–$C_6$alkynyl or phenyl, unsubstituted or substituted by halogen, nitro, cyano, $C_1$–$C_4$alkyl or by $C_1$–$C_4$alkoxy, and
$R_{19}$ and $R_{20}$ are identical or different and are each independently of the other hydrogen or $C_1$–$C_4$alkyl (sub-group Bc).

Another preferred group is formed by compounds of formula I wherein
n is a number one;
$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group NR$_{11}$R$_{12}$;
wherein $R_{11}$ and $R_{12}$ are each independently of the other $C_1$–$C_6$alkyl or together are tetra- or penta-methylene;
$R_2$ is hydrogen; and
$R_3$ is $C_3$–$C_7$cycloalkyl that is unsubstituted or may be substituted by $C_1$–$C_6$alkyl;
$R_4$, $R_5$, $R_6$ and $R_7$ are identical or different and are each independently of the others hydrogen or $C_1$–$C_4$alkyl;
$R_8$ is $C_1$–$C_6$alkyl;
$R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

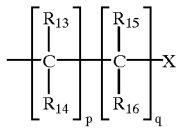

wherein
p is a number zero or one; and
q is a number zero; and
$R_{13}$ and $R_{14}$ are identical or different and are each independently of the other hydrogen or $C_1$–$C_4$alkyl; and
X is hydrogen, in which case p must have the value zero; phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; —COOR$_{17}$; —COR$_{18}$ or a group

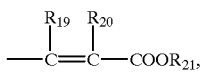

wherein
$R_{17}$ and $R_{21}$ are $C_1$–$C_6$alkyl, and
$R_{18}$ is hydrogen; $C_1$–$C_6$alkyl or phenyl, unsubstituted or substituted by halogen, nitro, cyano, $C_1$–$C_4$alkyl or by $C_1$–$C_4$alkoxy, and
$R_{19}$ and $R_{20}$ are hydrogen (sub-group C).

Important compounds of sub-group C within the scope of formula I are those wherein
n is a number one;
$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group NR$_{11}$R$_{12}$;
wherein $R_{11}$ and $R_{12}$ are each independently of the other $C_1$–$C_6$alkyl or together are tetra- or penta-methylene;
$R_2$ is hydrogen; and
$R_3$ is $C_3$–$C_7$cycloalkyl that is unsubstituted or may be substituted by $C_1$–$C_6$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is a $C_1$–$C_6$alkyl, $C_3$–$C_6$alkenyl or $C_3$–$C_6$alkynyl group substituted by one or more halogen atoms; or a group

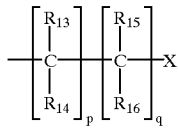

wherein p is a number one; and q is a number zero; and $R_{13}$ and $R_{14}$ are identical or different and are each independently of the other hydrogen or $C_1$–$C_4$alkyl; and X is phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$-cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; or —$COR_{18}$ and wherein $R_{18}$ is hydrogen or $C_1$–$C_4$alkyl (sub-group Ca).

An important sub-group comprises compounds of formula I wherein n is a number one;

$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$;

wherein $R_{11}$ and $R_{12}$ are each independently of the other $C_1$–$C_6$alkyl or together are tetra- or penta-methylene;

$R_2$ is hydrogen; and $R_3$ is $C_3$–$C_6$cycloalkyl that is unsubstituted or may be substituted by $C_1$–$C_6$alkyl;

$R_4$, $R_5$, $R_6$ and $R_7$ are identical or different and are each independently of the others hydrogen or $C_1$–$C_4$alkyl;

$R_8$ is $C_1$–$C_6$alkyl;

$R_9$ is a $C_1$–$C_6$alkyl or $C_3$–$C_6$alkenyl group substituted by one or more halogen atoms; or a group

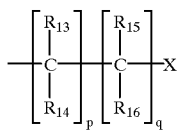

wherein p is a number one; and q is a number zero; and $R_{13}$ and $R_{14}$ are hydrogen; and X is phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$-cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; or —$COR_{18}$ and wherein $R_{18}$ is hydrogen or $C_1$–$C_4$alkyl (sub-group Cb).

A preferred sub-group comprises compounds of formula I wherein n is a number one;

$R_1$ is $C_1$–$C_6$alkyl; $C_2$–$C_4$alkenyl; $C_1$–$C_6$haloalkyl or a group $NR_{11}R_{12}$; wherein $R_{11}$ and $R_{12}$ are each independently of the other $C_1$–$C_2$alkyl;

$R_2$ is hydrogen; and $R_3$ is $C_3$–$C_6$cycloalkyl that is unsubstituted or may be substituted by $C_1$–$C_6$alkyl;

$R_4$ is hydrogen or $C_1$–$C_4$alkyl;

$R_5$, $R_6$ and $R_7$ are hydrogen;

$R_8$ is $C_1$–$C_2$alkyl;

$R_9$ is a $C_1$–$C_6$alkyl or $C_3$–$C_6$alkenyl group substituted by one or more halogen atoms; or a group

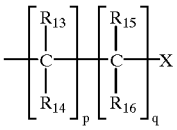

wherein p is a number one; and q is a number zero; and $R_{13}$ and $R_{14}$ are hydrogen; and X is phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$-cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; or —$COR_{18}$ and wherein $R_{18}$ is hydrogen or $C_1$–$C_4$alkyl (sub-group Cd).

Special mention should be made of compounds of sub-group Cd wherein n is a number one;

$R_1$ is $C_2$–$C_4$alkyl or dimethylamino;

$R_2$ is hydrogen; and $R_3$ is $C_3$–$C_6$cycloalkyl that is unsubstituted or may be substituted by $C_1$–$C_6$alkyl;

$R_4$, $R_5$, $R_6$ and $R_7$ are hydrogen;

$R_8$ is methyl;

$R_9$ is a $C_1$–$C_6$alkyl or $C_3$–$C_6$alkenyl group substituted by one or more halogen atoms; or a group

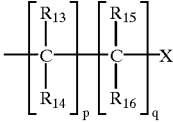

wherein p is a number one; and q is a number zero; and $R_{13}$ and $R_{14}$ are hydrogen; and X is phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$-cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; or —$COR_{18}$ and wherein $R_{18}$ is hydrogen or $C_1$–$C_4$alkyl (sub-group Ce).

In the above formula I, "halogen" includes fluorine, chlorine, bromine and iodine.

The alkyl, alkenyl and alkynyl radicals may be straight-chain or branched, and this applies also to the alkyl, alkenyl or alkynyl moiety of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl and the isomers thereof, for example isopropyl, isobutyl, tert-butyl or sec-butyl. Cycloalkyl is, depending upon the number of carbon atoms mentioned, cyclopropyl, cyclobutyl, cyclopentyl, cyclohexyl, cycloheptyl or cyclooctyl.

A haloalkyl group may have one or more (identical or different) halogen atoms, for example $CHCl_2$, $CH_2F$, $CCl_3$, $CH_2Cl$, $CHF_2$, $CF_3$, $CH_2CH_2Br$, $C_2Cl_5$, $CH_2Br$, $CHBrCl$ etc.

The presence of at least one asymmetric carbon atom and/or at least one asymmetric sulfur atom in the compounds of formula I means that the compounds may occur in optically isomeric forms. As a result of the presence of an aliphatic C=C double bond, geometric isomerism may also occur. The formula I is intended to include all those possible isomeric forms and mixtures thereof.

Certain α-amino acid derivatives having a different kind of structure have already been proposed for controlling plant-destructive fungi (for example in EP-398 072, EP-425 925, DE4 026 966, EP477 639, EP493 683, DE-4 035 851, EP487 154, EP496 239, EP-550 788 and EP-554 729). Those preparations are not satisfactory, however, in respect of their action. Surprisingly, with the compound structure of formula I, new kinds of microbicides having a high level of activity have been found.

DESCRIPTION OF THE PROCESS FOR THE PREPARATION OF COMPOUNDS ACCORDING TO THE INVENTION

The compounds of formula I can be prepared a) by reaction of a substituted amino acid of formula II

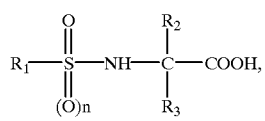

wherein the radicals $R_1$, $R_2$ and $R_3$ and n are as defined above, or a carboxy-activated derivative thereof, if desired in the presence of a catalyst, if desired in the presence of an acid-binding agent and if desired in the presence of a diluent, with an amine of formula III

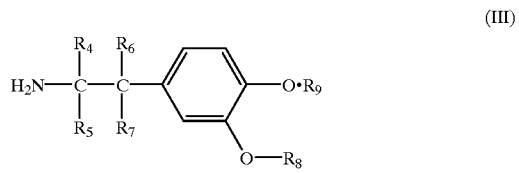

wherein $R_4$, $R_5$, $R_6$, $R_7$, $R_8$ and $R_9$ are as defined above.

The amino acid derivatives of formula II required for carrying out Process a) according to the invention are known per se or can be prepared in accordance with Process aa) described below.

The amines of formula III are generally known compounds of organic chemistry.

Suitable carboxy-activated derivatives of the amino acid of formula II include any carboxy-activated derivatives, such as acid halides, for example acid chlorides; also symmetrical or mixed anhydrides, for example the mixed O-alkylcarboxylic acid anhydrides; and also activated esters, for example p-nitrophenyl esters or N-hydroxysuccinimide esters, and activated forms of the amino acid produced in situ using condensation agents, e.g. dicyclohexylcarbodiimide, carbonyldiimidazole, O-(benzotriazol-1-yl)-N,N,N',N'-bis(penta-methylene) uronium hexafluorophosphate, O-(benzotriazol-1-yl)-N,N, N',N'-bis(tetra-methylene)uronium hexafluorophosphate, (benzotriazol-1-yloxy)-tripyrrolidinophosphonium hexafluorophosphate, (benzotriazol-1-yloxy)-tris (dimethylamino)phosphonium hexafluorophosphate or O-(benzotriazol-1-yl)-N,N,N',N'-tetramethyluronium hexafluorophosphate.

The acid halides corresponding to the amino acid of formula II can be prepared by reacting the amino acid of formula II in a manner known per se with a halogenating agent, for example phosphorus pentachloride, thionyl chloride, phosgene or oxalyl chloride.

The mixed anhydrides corresponding to the amino acid of formula II can be prepared by reacting the amino acid of formula II with a chloroformic acid ester, for example a chloroformic acid alkyl ester, preferably isobutyl chloroformate, if desired in the presence of an acid-binding agent, such as an inorganic or organic base, for example a tertiary amine, e.g. triethylamine, pyridine, N-methylpiperidine or N-methylmorpholine.

The reaction of the amino acid of formula II or of a carboxy-activated derivative of the amino acid of formula II, with an amine of formula III is carried out in an inert diluent. There may be mentioned as examples: aromatic, non-aromatic or halogenated hydrocarbons, for example chlorinated hydrocarbons, e.g. methylene chloride or toluene; ketones, e.g. acetone; esters, e.g. ethyl acetate; amides, e.g. dimethylformamide; nitrites, e.g. acetonitrile; or ethers, e.g. tetrahydrofuran, dioxane, diethyl ether or tert-butyl methyl ether; or water or mixtures of those inert diluents. Examples of acid-binding agents which may be present are inorganic and organic bases, for example an alkali metal or alkaline earth metal hydroxide or carbonate, e.g. sodium hydroxide, potassium hydroxide, sodium carbonate or potassium carbonate, or, for example, a tertiary amine, e.g. triethylamine, pyridine, N-methylpiperidine or N-methylmorpholine. The temperatures are from −80 to +150° C., preferably from −40 to +40° C.

Compounds of formula I can also be prepared
b) by oxidation of a compound of formula I'

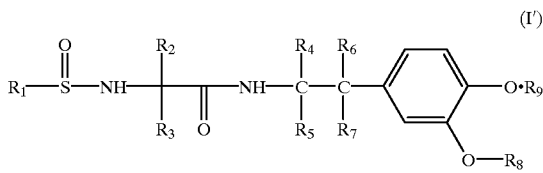

wherein $R_1$, $R_2$, $R_3$, $R_4$, $R_5$, $R_6$, $R_7$, $R_8$ and $R_9$ are as defined above, with the proviso that $R_3$ is not substituted by mercapto or $C_1$–$C_4$alkylthio.

Suitable oxidising agents include both organic oxidising agents, such as alkyl hydroperoxides, for example cumyl hydroperoxide, and inorganic oxidising agents, such as peroxides, for example hydrogen peroxide, and transition metal oxides, for example chromium trioxide, and transition metal oxide salts, for example potassium permanganate, potassium dichromate or sodium dichromate.

The reaction of a compound of formula I' with the oxidising agent is carried out in an inert diluent, such as water or a ketone, for example acetone, or in a mixture thereof, optionally in the presence of an acid or optionally in the presence of a base, at temperatures of from –80 to +150° C.

The compounds of formula I can also be prepared
c) by reaction of a compound of formula I"

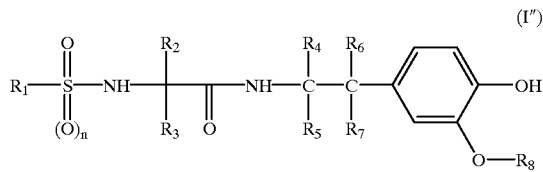

wherein $R_1$, $R_2$, $R_3$, $R_4$, $R_5$, $R_6$, $R_7$ and $R_8$ and n are as defined above, with a compound of formula VI

wherein $R_9$ is as defined above and wherein Y is a leaving group. Suitable leaving groups include halides, for example chlorides or bromides, and sulfonates, for example tosylates, mesylates or triflates.

The reaction of a compound of formula I" with a compound of formula VI is carried out in an inert diluent. The following may be mentioned as examples: aromatic, non-aromatic or halogenated hydrocarbons, e.g. methylene chloride ortoluene; ketones, e.g. acetone; esters, e.g. ethyl acetate; amides, e.g. dimethylformamide; nitriles, e.g. acetonitrile; ethers, e.g. tetrahydrofuran, dioxane, diethyl ether or tert-butyl methyl ether; alcohols, e.g. methanol, ethanol, n-butanol, isopropanol or tert-butanol; dimethyl suifoxide: or water; or mixtures of those inert diluents.

The reaction of a compound of formula I" with a compound of formula VI is carried out if desired in the presence of an acid-binding agent. Suitable acid-binding agents include inorganic or organic bases, for example alkali metal or alkaline earth metal hydroxides, alcoholates or carbonates, e.g. sodium hydroxide, potassium hydroxide, sodium methanolate, potassium methanolate, sodium ethanolate, potassium ethanoiate, sodium tert-butanolate, potassium tert-butanolate, sodium carbonate or potassium carbonate. The temperatures are from –80 to +200° C., preferably from 0 to +120° C.

aa) The required amino acid derivatives of formula II can be prepared by reaction of an amino acid of formula VII

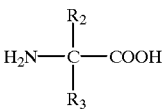

wherein $R_2$ and $R_3$ are as defined above, with a sulfonic acid or sulfinic acid, or with a sulfonic acid or sulfinic acid derivative, of formula IV

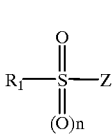

wherein $R_1$ and n are as defined above and wherein Z is an OH group or a leaving group, respectively.

The sulfonic acid or sulfinic acid, or sulfonic acid or sulfinic acid derivative, of formula IV required for Process aa) and the amino acids of formula VI are known per se.

Suitable sulfonic acid or sulfinic acid derivatives of formula IV include any compounds wherein Z is a leaving group, such as sulfonic acid halides or sulfinic acid halides, e.g. sulfochlorides or sulfinic acid chlorides; also symmetrical or mixed anhydrides; and also activated forms of sulfonic acid or sulfinic acid produced in situ using condensation agents, such as dicyclohexylcarbodiimide or carbonyidiimidazole.

The compounds of formula I are stable oils or solids at room temperature that are distinguished by valuable microbicidal properties. They can be used in the agricultural sector or related fields preventively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy pests that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be preferentially effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Bremia, Pythium, Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method for the treatment of plants which comprises the application of the novel compounds of formula I or the novel compositions.

Target crops to be protected within the scope of this invention comprise, for example, the following species of plants: cereals (wheat, barley, rye, oats, rice, maize, sorghum, spelt, triticale and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally applied in the form of compositions and can be applied to the area or plant to be treated simultaneously or in succession with other active ingredients. Those further active ingredients may be fertilisers, micronutrient donors or other preparations that influence plant growth. It is also possible to use selective herbicides and also insecticides, fungicides, bactericides, nematicides, molluscicides or mixtures of several of those preparations, if desired together with further carriers, surfactants or other application-promoting adjuvants customarily employed in formulation technology.

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binders or fertilisers.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to propagation material (grains, fruits, tubers, shoots, cuttings, roots, etc.) (dressing) either by impregnating, for example, cereal grains (seed) or potato tubers or freshly cut shoots with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound (active ingredient) of formula I and, where appropriate, a solid or liquid adjuvant are prepared in known manner, e.g. by homogeneously mixing and/or grinding the active ingredient with extenders and adjuvants customary in agricultural technology, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers, micronutrient donors or other preparations that influence plant growth for obtaining special effects.

The compounds of formula I can be mixed with other fungicides, with the result that in some cases unexpected synergistic effects are obtained. Especially preferred mixing partners are azoles, such as propiconazole, difenoconazole, cyproconazole, epoxiconazole, tebuconazole, tetraconazole, fenbuconazole, metconazole, bromuconazole; also fenpropidine, fenpropimorph, cyprodinil, pyrimethanil, benzo-1,2,3-thiadiazole-7-carbonothioic acid S-methyl ester, and strobilurins, such as azoxystrobin and cresoxime-methyl.

The Examples which follow illustrate the invention described above, without limiting the scope thereof in any way. Temperatures are given in degrees Celsius.

Prepararation Examples for Compounds of Formula

P-1.1:(R,S)-α-(Ethylsulfonyulamino)-cyclohexaneacetic acid N-[2-(4-hydroxy-3-methoxyphenyl)-ethyl]-amide [Comp. 1.1]

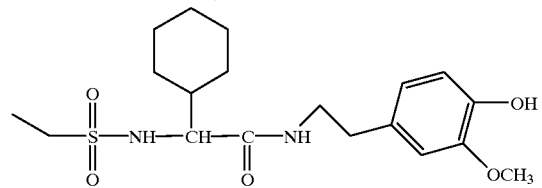

A mixture of 12.3 g of (R,S)-α-(ethylsulfonylamino)-cyclohexaneacetic acid, 10.1 g of 2-(4-hydroxy-3-methoxyphenyl)-ethylamine, 21.8 g of (benzotriazol-1-yloxy)-tris(dimethylamino)-phosphonium hexafluorophosphate and 51 ml of N-ethyl-diisopropyiamine is stirred in 250 ml of N,N-dimethylformamide at room temperature for 4 hours. The reaction mixture is then introduced into 500 ml of water. Extraction is carried out twice using 400 ml of ethyl acetate each time. The organic phases are washed with 400 ml of saturated sodium chloride solution, combined, dried over magnesium sulfate and concentrated, yielding (R,S)-α-(ethylsulfonylamino)-cyclohexaneacetic acid N-[2-(4-hydroxy-3-methoxyphenyl)-ethyl]-amide in the form of a resin, which can be purified by chromatography on silica gel with ethyl acetate/n-hexane.

The compounds listed in Table 1 are prepared analogously to the above Example.

TABLE 1

Structure: $R_1-S(O)_n(O_2)-NH-C(R_2)(R_3)-C(O)-NH-CH(R_4)-CH_2-\text{[3-methoxy-4-}OR_9\text{-phenyl]}$

| Comp. No. | n | $R_1$ | $R_2$ | $R_3$ | $R_4$ | $R_9$ | Conf. α-C | Phys. data m.p. °C |
|---|---|---|---|---|---|---|---|---|
| 1.1 | 1 | ethyl | H | cyclohexyl | H | H | (R, S) | resin |
| 1.2 | 1 | ethyl | H | cyclohexyl | H | benzyl | (R, S) | |
| 1.3 | 1 | ethyl | H | cyclohexyl | Me | H | (R, S) | |
| 1.4 | 1 | ethyl | H | cyclohexyl | Me | benzyl | (R, S) | |
| 1.5 | 1 | $N(Me)_2$ | H | cyclohexyl | H | H | (R, S) | |
| 1.6 | 1 | $N(Me)_2$ | H | cyclohexyl | H | benzyl | (R, S) | |
| 1.7 | 1 | methyl | H | cyclopropyl | H | H | (R, S) | |
| 1.8 | 1 | methyl | H | cyclopropyl | H | benzyl | (R, S) | |
| 1.9 | 1 | ethyl | H | cyclopropyl | H | H | (R, S) | resin |
| 1.10 | 1 | ethyl | H | cyclopropyl | H | benzyl | (R, S) | |
| 1.11 | 1 | ethyl | H | cyclopropyl | H | acetyl | (R, S) | |
| 1.12 | 1 | ethyl | H | cyclopropyl | H | benzoyl | (R, S) | |
| 1.13 | 1 | ethyl | H | cyclopropyl | H | H | (S) | |
| 1.14 | 1 | ethyl | H | cyclopropyl | H | benzyl | (S) | |
| 1.15 | 1 | n-propyl | H | cyclopropyl | H | H | (R, S) | |
| 1.16 | 1 | n-propyl | H | cyclopropyl | H | benzyl | (R, S) | |
| 1.17 | 1 | 3-chloropropyl | H | cyclopropyl | H | H | (R, S) | |
| 1.18 | 1 | 3-chloropropyl | H | cyclopropyl | H | benzyl | (R, S) | |
| 1.19 | 1 | n-butyl | H | cyclopropyl | H | H | (R, S) | |
| 1.20 | 1 | n-butyl | H | cyclopropyl | H | benzyl | (R, S) | |
| 1.21 | 1 | isopropyl | H | cyclopropyl | H | H | (R, S) | |
| 1.22 | 1 | isopropyl | H | cyclopropyl | H | benzyl | (R, S) | |
| 1.23 | 0 | isopropyl | H | cyclopropyl | H | H | (R, S) | |
| 1.24 | 0 | isopropyl | H | cyclopropyl | H | benzyl | (R, S) | |
| 1.25 | 1 | ethyl | Me | cyclopropyl | H | H | (R, S) | |
| 1.26 | 1 | ethyl | Me | cyclopropyl | H | benzyl | (R, S) | |
| 1.27 | 1 | $N(Me)_2$ | H | cyclopropyl | H | H | (R, S) | |
| 1.28 | 1 | $N(Me)_2$ | H | cyclopropyl | H | benzyl | (R, S) | |
| 1.29 | 1 | ethyl | H | cyclopentyl | H | H | (R, S) | |
| 1.30 | 1 | ethyl | H | cyclopentyl | H | benzy | (R, S) | |
| 1.31 | 1 | $N(Me)_2$ | H | cyclopentyl | H | H | (R, S) | |
| 1.32 | 1 | $N(Me)_2$ | H | cyclopentyl | H | benzyl | (R, S) | |
| 1.33 | 1 | ethenyl | H | cyclopropyl | H | H | (R, S) | |
| 1.34 | 1 | ethenyl | H | cyclopropyl | H | benzyl | (R, S) | |
| 1.35 | 0 | $MeOOC-CH_2$ | H | cyclopropyl | H | benzyl | (R, S) | |
| 1.36 | 1 | $MeOOC-CH_2$ | H | cyclopropyl | H | benzyl | (R, S) | |
| 1.37 | 1 | $MeOOC-CH_2$ | H | cyclopropyl | H | H | (R, S) | |
| 1.38 | 1 | $CF_3$ | H | cyclopropyl | H | benzyl | (R, S) | |
| 1.39 | 1 | $CF_3$ | H | cyclopropyl | H | H | (R, S) | |
| 1.40 | 0 | ethyl | H | cyclopropyl | H | benzyl | (R, S) | |
| 1.41 | 0 | ethyl | H | cyclopropyl | H | 3,4-diCl-benzyl | (R, S) | |
| 1.42 | 0 | ethyl | H | cyclopropyl | H | 3-Cl-benzyl | (R, S) | |

P-2:(R,S)-α-(Ethylsulfonylamino)-cyclohexaneacetic acid N-{2-[4-(3,4-dichlorobenzyloxy)-3-methoxyphenyl]-ethyl}-amide
[Comp. 2.1]

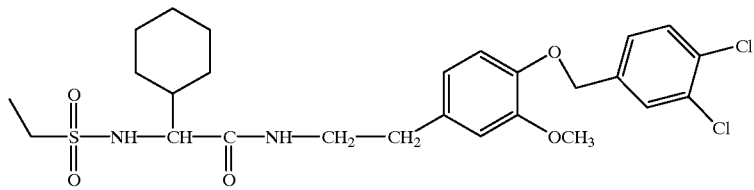

A mixture of 2.8 g of (R,S)-α-(ethylsulfonylamino)-cyclohexaneacetic acid N-[2-(4-hydroxy-3-methoxyphenyl)-ethyl]-amide, 1.3 ml of 3,4-dichlorobenzyl chloride and 26 ml of 1N sodium methanolate solution in methanol is heated in 50 ml of methanol at reflux for 16 hours. After cooling, the reaction mixture is introduced into 200 ml of 2N sodium hydroxide solution. Extraction is carried out twice using 300 ml of diethyl ether each time. The organic phases are washed once with 200 ml of saturated sodium chloride solution, dried over magnesium sulfate and concentrated, yielding (R,S)-α-(ethylsulfonylamino)-cyclohexaneacetic acid N-{2-[4-(3,4-dichlorobenzyloxy)-3-methoxyphenyl]-ethyl}-amide, which can be purified by chromatography on silica gel with ethyl acetate/n-hexane=2:1 and subsequent recrystallisation from ethyl acetatein-hexane. Melting point 164–165° C.

The Examples listed in Table 2 are obtained in analogous manner.

TABLE 2

| Comp. No. | $R_1$ | $R_3$ | $R_9$ | Phys. data m.p. ° C. |
|---|---|---|---|---|
| 2.1 | ethyl | cyclohexyl | 3,4-dichlorobenzyl | 164–165 |
| 2.2 | N(Me)$_2$ | cyclohexyl | 3,4-dichlorobenzyl | |
| 2.3 | methyl | cyclohexyl | 3,4-dichlorobenzyl | |
| 2.4 | ethyl | cyclohexyl | 3-chlorobenzyl | |
| 2.5 | ethyl | cyclohexyl | 3-CF$_3$-benzyl | |
| 2.6 | ethyl | cyclohexyl | 4-methylbenzyl | |
| 2.7 | ethyl | cyclohexyl | 2-chlorobenzyl | |
| 2.9 | ethyl | cyclopentyl | 3,4-dichlorobenzyl | |
| 2.10 | ethyl | cyclopentyl | 3-CF$_3$-benzyl | |
| 2.11 | ethyl | cyclopropyl | 3,4-dichlorobenzyl | 135–136 |
| 2.12 | isopropyl | cyclopropyl | 3,4-dichlorobenzyl | |
| 2.13 | 3-Cl-propyl | cyclopropyl | 3,4-dichlorobenzyl | |
| 2.14 | N(Me)$_2$ | cyclopropyl | 3,4-dichlorobenzyl | |
| 2.15 | ethyl | cyclopropyl | 4-chlorobenzyl | |
| 2.16 | ethyl | cyclopropyl | 3-chlorobenzyl | |
| 2.17 | ethyl | cyclopropyl | 3,4-dichlorobenzyl | |
| 2.18 | ethyl | cyclopropyl | 2-chlorobenzyl | |
| 2.19 | ethyl | cyclopropyl | 4-methylbenzyl | |
| 2.20 | ethyl | cyclopropyl | 2-methylbenzyl | |
| 2.21 | ethyl | cyclopropyl | 4-nitrobenzyl | |
| 2.22 | ethyl | cyclopropyl | 4-cyanobenzyl | |
| 2.23 | ethyl | cyclopropyl | 4-CF$_3$-benzyl | |
| 2.24 | ethyl | cyclopropyl | 3-CF$_3$-benzyl | |
| 2.25 | ethyl | cyclopropyl | 4-difluoromethoxy-benzyl | |
| 2.26 | ethyl | cyclopropyl | 4-MeS-benzyl | |
| 2.27 | ethyl | cyclopropyl | 4-methoxycarbonyl-benzyl | |
| 2.28 | ethyl | cyclopropyl | 3-Cl-prop-2-en-1-yl | |
| 2.29 | ethyl | cyclopropyl | 2-Cl-prop-2-en-1-yl | |
| 2.30 | ethyl | cyclopropyl | 3-phenyl-prop-2-en-1-yl | |
| 2.31 | ethyl | cyclopropyl | cyanomethyl | |
| 2.32 | ethyl | cyclopropyl | (methoxycarbonyl)-methyl | |
| 2.33 | ethyl | cyclopropyl | cyclopentyl | |

Preparation Example for Intermediates

I 1.1:(R,S)-α-(Ethylsulfonylamino)-cyclohexaneacetic acid [Comp. 3.1]

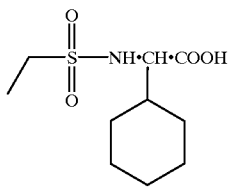

35.6 g of (R,S)-α-amino-cyclohexaneacetic acid hydrochloride and 14.7 g of sodium hydroxide are dissolved in 200 ml of water and cooled to 0° C. There are then added drop-wise to that mechanically stirred solution, simultaneously over a period of 1 hour, a solution of 7.4 g of sodium hydroxide in 90 ml of water and a solution of 17.4 ml of ethanesulfochloride in 200 ml of toluene. Stirring is then continued at 0° C. for 2 hours and then at room temperature for 4 hours. The reaction mixture is then extracted twice using 250 ml of toluene each time. The organic phases are washed once with 200 ml of 2N sodium hydroxide solution. The combined aqueous extracts are adjusted to pH<3 by the addition of 50 ml of conc. hydrochloric acid. Extraction is then carried out twice using 300 ml of ethyl acetate each time. The organic phases are washed with 200 ml of saturated sodium chloride solution, combined, dried over magnesium sulfate and concentrated, yielding (R,S)-α-(ethylsulfonylamino)-cyclohexaneacetic acid in the form of an oil.

TABLE 3

| Comp. No. | n | $R_1$ | $R_2$ | $R_3$ | Conf. α-C | Phys. data |
|---|---|---|---|---|---|---|
| 3.1 | 1 | ethyl | H | cyclohexyl | (R, S) | oil |
| 3.2 | 1 | N(Me)$_2$ | H | cyclohexyl | (R, S) | |
| 3.3 | 1 | methyl | H | cyclohexyl | (R, S) | |
| 3.4 | 1 | methyl | H | cyclopropyl | (R, S) | |
| 3.5 | 1 | ethyl | H | cyclopropyl | (R, S) | oil |
| 3.6 | 1 | ethyl | H | cyclopropyl | (S) | |
| 3.7 | 1 | n-propyl | H | cyclopropyl | (R, S) | |
| 3.8 | 1 | 3-chloropropyl | H | cyclopropyl | (R, S) | |
| 3.9 | 1 | n-butyl | H | cyclopropyl | (R, S) | |
| 3.10 | 1 | isopropyl | H | cyclopropyl | (R, S) | |
| 3.11 | 0 | isopropyl | H | cyclopropyl | (R, S) | |
| 3.12 | 1 | ethyl | Me | cyclopropyl | (R, S) | |
| 3.13 | 1 | N(Me)$_2$ | H | cyclopropyl | (R, S) | |
| 3.14 | 1 | ethyl | H | cyclopentyl | (R, S) | |
| 3.15 | 1 | N(Me)$_2$ | H | cyclopentyl | (R, S) | |

2. Formulation Examples for Compounds of Formula I (Throughout, Percentages are by Weight)

| F-2.1. Wettable powders | a) | b) | c) |
|---|---|---|---|
| a compound of Tables 1 and 2, e.g. Comp. 2.11 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |

| F-2.1. Wettable powders | a) | b) | c) |
|---|---|---|---|
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

| F-2.2. Emulsifiable concentrate | |
|---|---|
| a compound of Tables 1 and 2, e.g. 2.11 | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required concentration can be obtained from this concentrate by dilution with water.

| F-2.3. Dusts | a) | b) |
|---|---|---|
| a compound of Tables 1 and 2 | 5% | 8% |
| talcum | 95% | — |
| kaolin | — | 92% |

Ready-for-use dusts are obtained by mixing the active ingredient with the carrier and grinding the mixture in a suitable mill.

| F-2.4 Extruder granules | |
|---|---|
| a compound of Tables 1 and 2 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| F-2.5. Coated granules | |
|---|---|
| a compound of Tables 1 and 2 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| F-2.6. Suspension concentrate | |
|---|---|
| a compound of Tables 1 and 2, e.g. Comp. 2.11 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired dilution can be obtained by dilution with water.

BIOLOGICAL EXAMPLES

B-1: Action against *Plasmopara viticola* on vines a) Residual-Protective Action Vine seedlings are sprayed at the 4- to 5-leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-Curative Action

Vine seedlings are infected at the 4- to 5-leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 and 2 exhibit a very good fungicidal action against *Plasmopara viticola* on vines. Compounds Nos. 2.1 and 2.11 achieve complete suppression of fungus infestation (residual infestation 0 to 5%). On the other hand, Plasmopara infestation on untreated and infected control plants is 100%.

B-2: Action Against Phytophthora on Tomato Plants a) Residual-Protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 4 days, the treated plants are infected with a sporangia suspension of the fungus. Fungus infestation is evaluated after incubation of the infected plants for 4 days at 90–100% relative humidity and 20° C.

Compounds of Tables 1 and 2 exhibit a lasting effect (less than 20% fungus infestation). Infestation is prevented virtually completely (0 to 5% infestation) with compounds Nos. 2.1 and 2.11. On the other hand, Phytophthora infestation on untreated and infected control plants is 100%.

B-3: Action Against Phytophthora on Potato Plants a) Residual-Protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and 20° C.

Compounds of Tables 1 and 2 exhibit a lasting effect (less than 20% fungus infestation). Infestation is prevented virtually completely (0 to 5% infestation) with compounds Nos. 2.1 and 2.11. On the other hand, Phytophthora infestation on untreated and infected control plants is 100%.

What is claimed is:

1. A compound of formula I

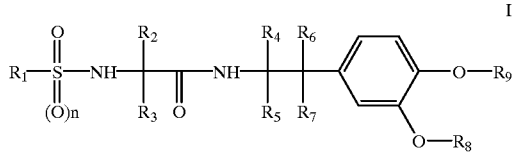

wherein the substituents are defined as follows:
n is a number zero or one;
$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl, $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl or a group $NR_{11}R_{12}$; wherein $R_{11}$ and $R_{12}$ are each independently of the other hydrogen, $C_1$–$C_6$alkyl or together are tetra- or penta-methylene;
$R_2$ is hydrogen, $C_1$–$C_8$alkyl;
$R_3$ is $C_3$–$C_8$cycloalkyl that is unsubstituted or may be substituted by $C_1$–$C_6$alkyl, hydroxy, $C_1$–$C_4$alkoxy, mercapto or by $C_1$–$C_4$alkylthio;
$R_4$, $R_5$, $R_6$ and $R_7$ are identical or different and are each independently of the others hydrogen or $C_1$–$C_4$alkyl;
$R_8$ is $C_1$–$C_6$alkyl, $C_3$–$C_6$alkenyl or $C_3$–$C_6$alkynyl;
$R_9$ is $C_3$–$C_8$cycloalkyl; a $C_1$–$C_6$alkyl-, $C_3$–$C_6$alkenyl- or $C_3$–$C_6$alkynyl-group each of which is substituted by one or more halogen atoms; or a group

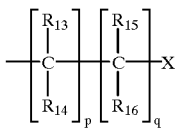

wherein
p and q are identical or different and are each independently of the other a number zero or one; and
$R_{13}$, $R_{14}$, $R_{15}$ and $R_{16}$ are identical or different and are each independently of the others hydrogen or $C_1$–$C_4$alkyl;
X is hydrogen, in which case p and q must have the value zero; phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$-haloalkoxy, $C_1$–$C_6$-alkylthio, $C_1$–$C_6$alkoxycarbonyl, $C_3$–$C_6$alkenyloxycarbonyl, $C_3$–$C_6$alkynyloxy-carbonyl, $C_1$–$C_6$-alkyl or by $C_1$–$C_6$alkoxy; cyano; —COOR$_{17}$; —COR$_{18}$ or a group

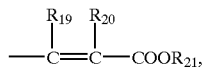

wherein
$R_{17}$ and $R_{21}$ are each independently of the other hydrogen, $C_1$–$C_6$alkyl, $C_3$–$C_6$alkenyl or $C_3$–$C_6$alkynyl, and
$R_{18}$ is hydrogen; $C_1$–$C_6$alkyl, $C_2$–$C_6$alkenyl, $C_2$–$C_6$alkynyl or phenyl, unsubstituted or substituted by halogen, nitro, cyano, $C_1$–$C_4$alkyl or by $C_1$–$C_4$alkoxy, and
$R_{19}$ and $R_{20}$ are identical or different and are each independently of the other hydrogen or $C_1$–$C_4$alkyl.

2. A compound of formula I according to claim 1, wherein
n is a number one;
$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group $NR_{11}$, $R_{12}$;
wherein $R_{11}$ and $R_{12}$ are each independently of the other hydrogen, $C_1$–$C_6$alkyl or together are tetra- or penta-methylene;
$R_2$ is hydrogen; and
$R_3$ is $C_3$–$C_7$cycloalkyl that is unsubstituted or may be substituted by $C_1$–$C_6$alkyl.

3. A compound of formula I according to claim 1, wherein $R_8$ is $C_1$–$C_6$alkyl.

4. A compound of formula I according to claim 1, wherein
$R_1$ is $C_1$–$C_{12}$alkyl; $C_1$–$C_{12}$haloalkyl or a group $NR_{11}R_{12}$; wherein $R_{11}$ and $R_{12}$ are $C_1$–$C_6$alkyl;
$R_4$ is hydrogen or $C_1$–$C_4$alkyl;
$R_5$, $R_6$ and $R_7$ are hydrogen.

5. A compound of formula I according to claim 1, wherein
$R_1$ is $C_2$–$C_4$alkyl or dimethylamino;
$R_3$ is cyclopropyl, unsubstituted or substituted by $C_1$–$C_4$alkyl;
$R_4$ is hydrogen;
$R_8$ is methyl.

6. A compound of formula I according to claim 3, wherein $R_9$ is $C_3$–$C_8$cycloalkyl; a $C_1$–$C_6$alkyl, $C_3$–$C_6$alkenyl or $C_3$–$C_6$alkynyl group substituted by one or more halogen atoms; or a group

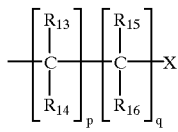

wherein
p is a number zero or one; and
q is a number zero; and
$R_{13}$ and $R_{14}$ are identical or different and are each independently of the other hydrogen or $C_1$–$C_4$alkyl; and
X is hydrogen, in which case p must have the value zero; phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalkoxy, $C_1$–$C_6$alkylthio, $C_1$–$C_6$alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy; cyano; —$COOR_{17}$; —$COR_{18}$ or a group

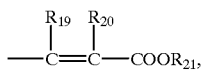

wherein
$R_{17}$ and $R_{21}$ are $C_1$–$C_6$alkyl, and
$R_{18}$ is hydrogen; $C_1$–$C_6$alkyl or phenyl, unsubstituted or substituted by halogen, nitro, cyano,
$C_1$–$C_4$alkyl or by $C_1$–$C_4$alkoxy, and
$R_{19}$ and $R_{20}$ are hydrogen.

7. A compound of formula I according to claim 6, wherein
$R_3$ is $C_3$–$C_6$cycloalkyl that is unsubstituted or may be substituted by $C_1$–$C_6$alkyl;
$R_9$ is a $C_1$–$C_6$alkyl or $C_3$–$C_6$alkenyl group substituted by one or more halogen atoms; or a group

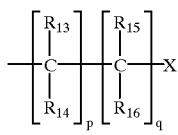

wherein
p is a number one; and
q is a number zero; and
$R_{13}$ and $R_{14}$ are hydrogen; and
X is phenyl, unsubstituted or mono- or poly-substituted by halogen, nitro, cyano, carboxy, $C_2$–$C_6$alkenyl, $C_2$–$C_6$alkynyl, $C_1$–$C_6$haloalkyl, $C_3$–$C_6$alkenyloxy, $C_3$–$C_6$alkynyloxy, $C_3$–$C_7$cycloalkyl, $C_1$–$C_6$haloalkoxy, $C_1$–$C_6$alkylthio, $C_1$–$C_6$ alkoxycarbonyl, $C_3$–$C_6$alkenyloxycarbonyl, $C_3$–$C_6$alkynyloxycarbonyl, $C_1$–$C_6$alkyl or by $C_1$–$C_6$alkoxy.

8. A compound of formula I according to claim 7, wherein
$R_1$ is $C_2$–$C_4$alkyl or dimethylamino;
$R_4$, $R_5$, $R_6$ and $R_7$ are hydrogen;
$R_8$ is methyl.

9. A process for the preparation of a compound of formula I according to claim 1, which process comprises a) reacting a substituted amino acid of formula II

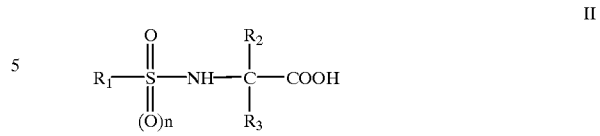

with an amine of formula III

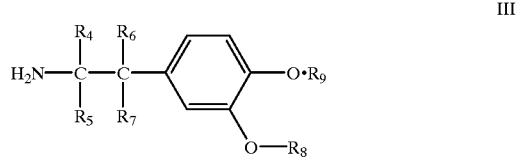

with or without diluent, if desired in the presence of an acid-binding agent at temperatures of from −80° C. to 150° C., or b) oxidising a compound of formula I'

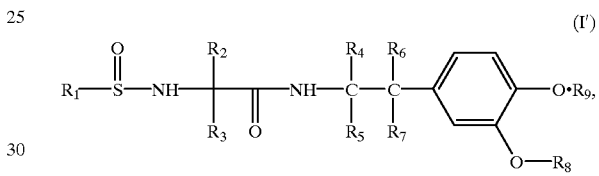

with the proviso that $R_3$ is not substituted by mercapto or $C_1$–$C_4$alkylthio, with an oxidising agent in a diluent, optionally in the presence of an acid or a base at temperatures of from −80° C. to 150° C., or c) reacting a compound of formula I"

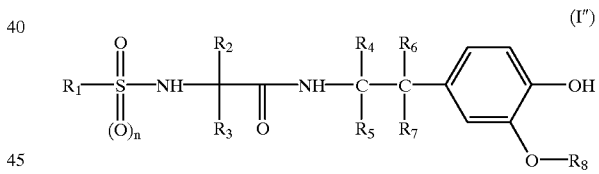

with a compound of formula VI

in a diluent, if desired in the presence of an acid-binding agent at temperatures of from −80 to 200° C.,
wherein, in the formulae II, III, VI, I' and I", the substituents $R_1$, $R_2$, $R_3$, $R_4$, $R_5$, $R_6$, $R_7$, $R_8$, $R_9$ and n are as defined for formula I and Y is halogen or a sulfonate.

10. A composition for controlling and preventing an infestation of plants by microorganisms, comprising a compound of formula I according to claim 1 as active ingredient together with a suitable carrier.

11. A method of controlling and preventing an infestation of plants by microorganisms, which comprises the application of a compound of formula I according to claim 1 as active ingredient to the plant, to parts of the plant or to the plant's nutrient medium.

* * * * *